United States Patent
Villuendas Yuste et al.

(10) Patent No.: US 9,310,249 B2
(45) Date of Patent: Apr. 12, 2016

(54) SPECTROPHOTOMETER FOR THE AUTOMATED OPTICAL CHARACTERIZATION OF SOLAR COLLECTOR TUBES AND METHOD FOR THE OPERATION THEREOF

(75) Inventors: Francisco Villuendas Yuste, Saragossa (ES); Carlos David Heras Vila, Saragossa (ES); David Izquierdo Núñez, Saragossa (ES); Rafael Alonso Esteban, Saragossa (ES); Iñigo Salinas Áriz, Saragossa (ES); Santiago Forcada Pardo, Saragossa (ES); Noelia Martinez Sanz, Seville (ES)

(73) Assignee: Abengoa Solar New Technologies, S.A., Sevilla (ES)

( * ) Notice: Subject to any disclaimer, the term of this patent is extended or adjusted under 35 U.S.C. 154(b) by 115 days.

(21) Appl. No.: 13/880,698
(22) PCT Filed: Oct. 19, 2011
(86) PCT No.: PCT/ES2011/000303
§ 371 (c)(1),
(2), (4) Date: Oct. 27, 2013
(87) PCT Pub. No.: WO2012/052578
PCT Pub. Date: Apr. 26, 2012

(65) Prior Publication Data
US 2014/0146305 A1   May 29, 2014

(30) Foreign Application Priority Data
Oct. 20, 2010   (ES) .................................. 201001348

(51) Int. Cl.
*G01J 3/02* (2006.01)
*H02S 50/15* (2014.01)
(Continued)

(52) U.S. Cl.
CPC .............. *G01J 3/0291* (2013.01); *G01N 21/55* (2013.01); *G01N 21/59* (2013.01); *H02S 50/15* (2014.12);
(Continued)

(58) Field of Classification Search
CPC ....... G01J 3/0291; G01N 21/55; G01N 21/59; G01N 2021/558; G01N 2021/5969; F24J 2/055; F24J 2/46; H02S 50/10; H02S 50/15
See application file for complete search history.

(56) References Cited

U.S. PATENT DOCUMENTS

| 4,669,873 A | 6/1987 | Wirz |
| 4,921,351 A | 5/1990 | Kohigashi et al. |

(Continued)

FOREIGN PATENT DOCUMENTS

| EP | 0840106 | 5/1998 |
| EP | 0961475 | 12/1999 |

(Continued)

OTHER PUBLICATIONS

ISR for related PCT/ES2011/000303 mailed Feb. 23, 2012 and its English translation.

*Primary Examiner* — Michael A Lyons
*Assistant Examiner* — Dominic J Bologna
(74) *Attorney, Agent, or Firm* — KilpatrickTownsend & Stockton LLP (57) ABSTRACT

The invention relates to a spectrophotometer for the automated optical characterization of solar collector tubes and to a method for the operation thereof, that measures the coefficient of transmission of the glass tube and of reflection of the metal tube. The device includes all the necessary components for taking said measurement, such as the optical bench supporting the tube, the standard or framework, and the optical modules for the device, a main module that generates the light bundles, a measuring module that measures the coefficient of transmission of the outer glass tube and the coefficient of reflection of the inner metal tube, a mechanical system of tube rotation, an electronic system of data acquisition and processing, an external computer for controlling the device and processing the data measured, and a system of communication between the device and the computer.

25 Claims, 4 Drawing Sheets

(51) Int. Cl.
*G01N 21/55* (2014.01)
*G01N 21/59* (2006.01)
*F24J 2/05* (2006.01)
*F24J 2/46* (2006.01)

(52) U.S. Cl.
CPC ............... *F24J 2/055* (2013.01); *F24J 2/4607* (2013.01); *F28F 2200/00* (2013.01); *G01N 2021/558* (2013.01); *G01N 2021/5969* (2013.01)

(56) References Cited

U.S. PATENT DOCUMENTS

| | | | |
|---|---|---|---|
| 5,502,799 A * | 3/1996 | Tsuji et al. | 345/600 |
| 5,815,254 A * | 9/1998 | Greene | 356/73 |
| 6,246,474 B1 * | 6/2001 | Cerni et al. | 356/335 |
| 6,559,941 B1 * | 5/2003 | Hammer | 356/319 |
| 2009/0213371 A1 | 8/2009 | Goodyer et al. | |
| 2010/0219327 A1 * | 9/2010 | Arbore | G01N 21/55 250/206 |
| 2011/0108720 A1 * | 5/2011 | Ford et al. | 250/262 |
| 2011/0231120 A1 * | 9/2011 | Nishikawa | H02S 50/10 702/60 |
| 2012/0010854 A1 * | 1/2012 | Ciocan | G01N 21/31 702/182 |
| 2014/0176179 A1 * | 6/2014 | Minami | F21S 8/006 324/761.01 |

FOREIGN PATENT DOCUMENTS

| | | |
|---|---|---|
| JP | 2000241247 | 9/2000 |
| JP | 2000241248 | 9/2000 |

* cited by examiner

SPECTROPHOTOMETER FOR THE AUTOMATED OPTICAL CHARACTERIZATION OF SOLAR COLLECTOR TUBES AND METHOD FOR THE OPERATION THEREOF

CROSS-REFERENCE TO RELATED APPLICATIONS

This application is the national stage of International Patent Application No. PCT/ES2011/000303, filed on Oct. 19, 2011, which claims priority from Spanish patent application No. P201001348, filed on Oct. 20, 2010, the disclosures of which are incorporated herein in their entireties.

TECHNICAL SECTOR OF THE INVENTION

The invention is encompassed within the sector of measuring apparatus, more specifically, in the sector of measuring apparatus or instruments for optical parameters, such as the coefficients of reflection and transmission in cylindrical surfaces.

The surfaces to be characterized are the absorbing tubes installed in solar collectors, normally composed of two concentric tubes: an inner metal tube, which coefficient of reflection is of interest, and an outer glass tube, which coefficient of transmission is of interest.

This device includes all the necessary components for taking said measurement, such as the optical bench supporting the tube, allowing the rotation thereof and the displacement of the optical measuring head, the optical head taking the measurements of reflection and transmission, the module that generates the optical bundles that measure transmission and reflection, the electronic system of data acquisition and processing, an external computer for controlling the device and exporting the data measured, and a system of communication between the device and the computer.

BACKGROUND OF THE INVENTION

Renewable energies collected from thermal solar energy have a significant technological and economic importance in the domestic and industrial sectors. We have thermoelectric solar plants with solar energy concentration by means of cylindrical-parabolic mirrors on solar collection tubes among the most important technologies.

These systems require a maximum absorption of solar energy and the lowest possible energy loss. With this purpose, these systems are configured in vacuum tubes or similar structures that reduce conduction and convection losses and have highly absorbable coatings that absorb solar energy and low emissivity characteristics to decrease energy loss due to thermal radiation in the far infrared spectrum, wherein selective absorbing coatings play an essential role in the performance of the system.

Due to the foregoing, having an appropriate characterization system for absorbing tubes that allows measuring their coefficients of transmission and reflection with spectral resolution (maximum energy absorption and minimum energy loss) and also ensuring the uniformity of these values at all points of the tube becomes relevant. To achieve this, the device must be capable of precisely measuring the extreme values of the coefficients of reflection and transmission (near zero or near the unit), with spectral precision (around 10 nm) in the wavelengths required by the different reference standards and in an automated manner along different points of the tube.

A device that takes a spectral measurement of this type is called a spectrophotometer.

U.S. Pat. No. 4,669,873, Jun. 2, 1987, describes a spectrophotometer that measures the light transmitted, reflected, or radiated on at least one object or layer. The light is taken through fiberglass cable formed by a fiber matrix from the measuring point to the spectrophotometer. The object of the patent is to allow a high number of measuring points, independent from each other, or of several objects based on one single measurement and one single system of analysis, maintaining the precision of the measurement. The system uses its spectroscopic light scattering device, so the light of each fiber is scattered in its wavelengths over different points with a CCD (charge-coupled device), for example, and for each fiber there is a different angle, and therefore, a different CCD. We therefore have an array of fibers during detection, each one with its own CCD, for the individual and simultaneous spectroscopy of the different sample points collected by the different fibers used.

U.S. Pat. No. 4,921,351 of May 1990 describes a spectrophotometer that measures the reflectance of an object using the light of a pulsed tube Xe lamp to emit several flashes within the measuring time and filter ambient light through a high-pass filter.

U.S. Pat. No. 5,815,254, September 1998, describes an apparatus with two measuring modes, one for transmittance and the other for reflectance. The apparatus consists of two optical channels with a detector in each optical channel that measures direct light and reference light. The advantage of using only two channels is that it allows us to have a compact device for the field. Optical channels are preferably formed by optical fibers, and may also be formed by lenses and mirrors. Light is only injected from a fiber to obtain the measurement of transmittance. For the measurement of reflectance, the object is illuminated from several fibers, all of which are positioned in a circumference and introduced at 45°, so the reflection of all the fibers is collected in one single fiber to take the signal to the detector.

U.S. Pat. No. 6,559,941 of May 2003 describes a UV-VIS spectrophotomer with a pulsed Xe light source and solid-state detectors. The dynamic range in the detectors is reduced by modifying the power emitted in the pulses of the light source and the width of the slit at the input of the monochromator. This patent refers to the spatial non-uniformity of the pulses generated in the lamp, which must be considered in the design of the detection to place solid-state detectors instead of photomultipliers.

Patent US2009/0213371A1, of August 2009, describes a spectrophotometer with two detectors. which different spectral ranges overlap to cover a greater spectral range than the spectral range of each one of them individually. It describes a main module containing the light generation and light detection electronics and optics, and a measuring or testing module, both of which are connected by means of two optical fibers. The main module may be connected by USB to a PC. The measuring module is custom manufactured for each different object shape, and are exchanged. It only projects the light on the sample and collects reflected light, which returns to the main module for its detection through the fiber. It uses fiber bundle. The diffraction network is placed in the detection part of the main module, so the detectors are placed in different positions to collect the spectrum corresponding to the exit angle of the diffraction network, that is to say, two detectors are used but the light bundle is not divided (to avoid losing power); instead, the spectrums are spatially separated with the exit angle of the diffraction network.

None of the aforementioned devices or any other similar one device fulfill the necessary requirements for the automated characterization of absorbing tubes for solar collectors, either due to range, sensitivity, and/or mechanical configuration.

DESCRIPTION OF THE INVENTION

Bench, spectrophotometer, and characterization method of absorbing tubes of solar collectors for the simultaneous and automated characterization of coefficients of reflection and transmission at any point of the tube.

The present invention takes into consideration the specific characteristics for a design that fulfills requirements such as appropriate automation, precision, measurement taking speed, sensitivity and dynamic range.

The device takes the measurement of the coefficient of transmission of the outer glass tube and of the coefficient of reflection of the inner metal tube. The device takes the measurements for different wavelengths determined by a monochromator that spectrally filters the light bundle obtained from a white light lamp. The measurements may be taken automatically at any point of the tube.

In order to automate the process of characterizing any point of the tube, the device incorporates a system of tube rotation that allows the rotation thereof in at least ±180°, and a system of linear displacement that allows displacing the measuring module along the entire length of the tube and beyond the length thereof to also allow the calibration of the spectrophotometer based on a framework.

In order to take the measurement of the transmission and the reflection in a simultaneous and independent manner, the device generates two light bundles, one for transmission and the other for reflection, obtained from the same light source and marked at different frequencies for their correct differentiation during detection. These two bundles are generated in the main module, which remains fixed on the measuring bench for the greater stability and durability of the light sources. The two light bundles are taken by means of two multimode optical fibers to the measuring module, wherein the measurements are taken and which is displaced along the length of the tube by means of the system of linear displacement.

In order to obtain a system with wavelength resolution, the illumination of the tube is carried out by means of the system of monochromator and white light covering the wavelength range wherein the characterization is desired to be obtained, preferably within the range of 300 nm to 2,500 nm (ultraviolet to near infrared), with a resolution defined by the size of the fiber collecting the light bundle. The device may take measurements of as many wavelengths as desired, with wavelength increments or steps that could range between 1 nm to several sets of ten nm, according to the reference standard applicable in each case. In order to obtain the spectral range covering ultraviolet and near infrared, the device implements two photodetectors with different overlapping spectral responses at each measuring point, to which the optical signal arrives at the same time by means of a bundle splitter. The system of data processing will determine the signal coming from each detector to be processed for each wavelength.

With the purpose of obtaining a stable measurement regarding power changes in the source and variations of the modes in the multimode fibers used in the spectrophotometer to direct the light towards the tube, the device takes the measurement of the coefficients of transmission and reflection of each point of the tube under measure simultaneously, while also taking the measurement of direct light (transmitted and reflected) with the corresponding reference measurements for each one of them in a simultaneous manner.

Since the distribution of modes will vary due to the modification to the position of the fiber when the measuring module moves from one point to another, and with the purpose of obtaining a stable measurement regarding variations in the distribution of optical power between the propagation modes of the multimode fibers, the optical systems measuring the transmission and reflection include a diaphragm, which is the same for the measurements of direct light and reference light.

With the purpose of ensuring that all the light passing through the tube is measured by the direct transmission light detectors, the optical system includes a lens with a diameter at least twice as large than the size of the bundle at the light collection point, so the correct focalization of the light on the measuring detectors regarding variations in the trajectory of the rays is ensured.

With the purpose of ensuring that all the light reflected by the tube is measured by the direct reflection light detectors, the optical system includes a lens having a diameter at least twice as large than the size of the bundle at the light collection point, so the correct focalization of the light on the measuring detectors regarding variations in the trajectory of the rays is ensured.

The focal and distance ratios of objects and images of the systems of optical reflection and transmission, both in terms of direct light measuring and reference measuring are such that the size of the focalized light bundle in the detectors is smaller than the size of the area sensitive to the detectors.

In order to obtain a highly sensitive measurement that allows obtaining values of the coefficients of reflection and transmission that are very small or very near the unit with accuracy, the acquisition system needs to have a sufficiently high signal-to-noise-ratio. Given that the background optical signal mainly comes from ambient light, which may be of great intensity, carrying out some type of processing to said signal that allows achieving a high signal-to-noise-ratio is indispensable. The most appropriate in this case is the digital processing of the signal by means of the application of some extraction algorithm, such as synchronous detection or lock-in. In order to carry out a processing of this type, the signal to be measured needs to be easily distinguishable from background noise, which is usually achieved by means of the application of some sort of modulation thereof. The system modulates the optical signal used as transmission channel and the optical signal used as reflection channel at a different frequency by means of a rotating helix or a chopper system.

Another of the indispensable characteristics in a device of this type is the possibility of managing and controlling a personal computer in a comfortable and flexible manner. In the case of the present invention, this is solved by means of communication via USB port.

The general scheme of the measuring device is the following:

A profile structure serving as an optical bench supporting the tube, the main module, the measuring module, the framework or standard, the system of tube rotation, and the system of linear displacement of the measuring module.

A main module wherein the two light bundles that measure the transmission and reflection are generated, formed by:

a white light source, preferably a Xe or halogen lamp a monochromator covering the spectral range desired to be characterized, preferably from 300 nm to 2,500 nm an optical system generating the two measuring optical channels, modulated at different frequencies, preferably by chopper technique and with a multimode fiber output Two multimode fibers that optically connect the main module, which remains fixed, to the measuring module, which is displaced along the length of the tube and the standard or framework.

A measuring module wherein the illumination of the tube and the measuring of the optical signals necessary to characterize the coefficients of transmission and reflection of the tube are carried out, formed by:

An optical system for taking the measurement of transmission, composed of elements such as lenses, bundle splitters, and diaphragms, along with the necessary mechanics and electronics for the correct characterization of the transmission of the glass tube.

An optical system for taking the measurement of reflection, composed of elements such as lenses, bundle splitters, and diaphragms, along with the necessary mechanics and electronics for the correct characterization of the reflection of the metal tube.

A digital circuit that carries out the acquisition and analog/digital conversion functions of the signals of interest.

The connection between the main module and the measuring module for the transmission of the measured electric signals and data, preferably a USB connection.

A linear slider that allows displacing the measuring unit along the length of the tube and the framework or standard.

A mechanical support system for the tube that enables the rotation of the tube in a controller manner in at least ±180°.

A system of communication with any personal computer having the appropriate measuring software, communication via USB port being in a preferred embodiment.

A central processing unit that controls the global operation of the system, selecting the electronic components corresponding to the channel used at each moment and governing internal and external communications.

The software to be installed in the computer to be used with the device, necessary to carry out the communication with the same and the subsequent processing of the information acquired. This processing includes the processing of the signal for the elimination of noise and the storage of the data obtained in the appropriate format.

One of the advantages and advances provided by the invention is the fact that the system is capable of taking measurements of transmittance and reflectance of the tubes in an automated manner at any point or points selected, with high spectral resolution and in spectral ranges configurable in a simple manner and adjusted to the applicable regulations in each case.

DESCRIPTION OF THE DRAWINGS

With the purpose of aiding a better comprehension of the characteristics of the invention, a set of figures representing the following in a merely indicative rather than limitative manner, accompany this specification.

In terms of the references used in the figures:
(1) Measuring bench
(2) Tube under test
(3) Framework or standard tube
(4) Measuring module
(5) Main module
(6) Electronic system of data acquisition with analog/digital converter
(7) Data processing and control computer
(8) Communication system
(9) Mechanical system of tube rotation
(10) Linear displacement unit
(11) Set of optical filters
(12) Optical channel that measures transmission
(13) Outer glass tube
(14) Optical channel that measures reflection
(15) Inner metal tube
(16) Monochromator
(17) White light source
(18) Optical signal modulation system by chopper
(19) Cable tray chain
(20) Collimation lens, transmission channel
(21) Transmission bundle splitter to obtain reference
(22) Collecting lens for the direct measuring of the transmission channel
(23) InGaAs detector for the direct measuring of the transmission channel
(24) Si detector for the direct measuring of the transmission channel
(25) Transmission bundle splitter for direct measuring
(26) Collecting lens for the reference measuring of the transmission channel
(27) Transmission bundle splitter for the reference measuring
(28) InGaAs detector for the reference measuring of the transmission channel
(29) Si detector for the reference measuring of the transmission channel
(30) Focalization lens for the reflection channel
(31) Collecting lens for the direct measuring of the reflection channel
(32) Reflection bundle splitter for direct measuring
(33) InGaAs detector for the direct measuring of the reflection channel
(34) Si detector for the direct measuring of the reflection channel
(35) Collecting lens for the reference measuring of the reflection channel
(36) Reflection bundle splitter for reference measuring
(37) InGaAs detector for the reference measuring of the reflection channel (38) Si detector for the reference measuring of the reflection channel
(39) Modulation signals
(40) Measured analog electrical signals
(41) Control by means of digital output
(42) Reflection bench
(43) Transmission bench
(44) Window for the passage of the reflection bundle
(45) Light bundle that measures transmission
(46) Light bundle that measures reflection
(47) Commands
(48) Data
(49) Bundle splitter
(50) Diaphragm Preferred Embodiment of the Invention According to a preferred embodiment, the device comprises a measuring bench (1), wherein the tube under test (2) is placed, and a spectrophotometer formed by: a measuring module (4) that takes the measurements of the coefficients of reflection and transmission, a main module (5) that generates the optical bundles for the two light channels, reflection and transmission, an electronic system of data acquisition and processing with an analog/digital converter (6), and external computer (7), and a system of communication (8) between the device and said computer, preferably arranged as detailed in FIG. 1.

The tube under test (2) is placed on the measuring bench (1) in such a way that it is fastened by its extremities to bearings and a rotation system (9) that allow the rotation of the tube at an angle of at least 180°. A linear displacement unit (10) supports the measuring module (4) by the lower part of the tube (2) in such a way that the measuring module (4) may be displaced along the length of the tube under test (2) and also reach the area of the measuring bench (1), wherein a framework tube (3) is placed, allowing the correct calibration of the measurements. Depending on the position of the measuring module (4) and the rotation position of the tube under test (2), the device may take the measurements of the coefficients of reflection and transmission at any point or points of the tube (2) in an automated manner.

The optical system is a key section of the proposed device because it must enable the taking of a simultaneous measurement of the tubes in transmission and reflection with the precision and comfort required. In order to achieve the following, we propose a preferred embodiment according to the scheme of FIG. 2, which details the scheme of the spectrophotometer.

Figure 2:
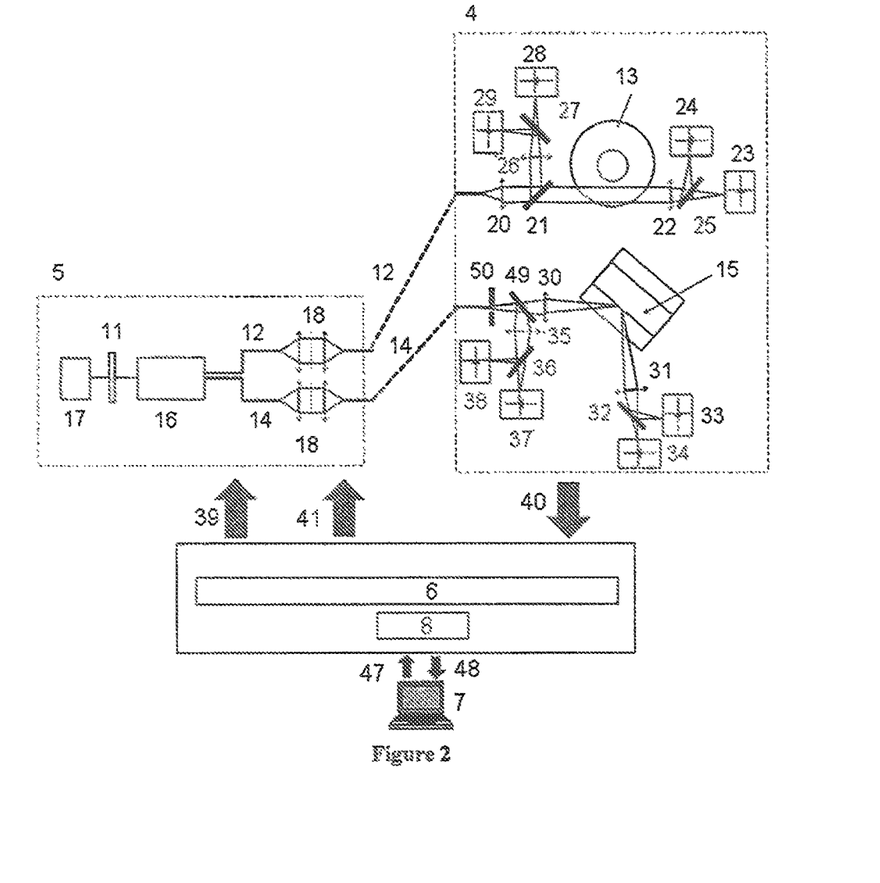
FIG. 2 represents a scheme of the measuring device of the proposed embodiment, including the optical system and the electronic components, as well as the data acquisition card that performs the analog/digital conversion functions of the signals and the communication with the PC.

The spectrophotometer includes, within the main module (5), two light channels, a first channel that measures the transmittance (12) of the outer glass tube (13), and a second channel that measures the reflectance (14) of the inner metal tube (15). The two light channels are generated from the output light bundle of a monochromator (16) that selects the desired wavelength on the light signal coming from a single white light source (17), which may be a Xe lamp or a halogen lamp. A set of filters (11) that are converting ensure the elimination of harmonics in the spectral range of measurement at the input of the monochromator.

In other to achieve a high signal-to-noise ratio in the measuring of the signals, the most appropriate course of action is the processing of the signal by means of the application of an extraction algorithm, such as synchronous detection or lock-in. To carry out a processing of this type, the signal to be measured needs to be easily distinguishable from background noise, which is usually achieved by means of the application of some sort of modulation thereof. To achieve the foregoing, each light channel (12, 14) is modulated in intensity at a different low modulation frequency (39) by means of a chopper (18), so synchronous detection or individual lock-in is implemented for each channel. This way, the measuring of the coefficients of reflection and transmission is simultaneous and free from the influence of ambient light. This processing is carried out digitally in the computer (7), for which the prior conversion of the analog signals by means of the acquisition card (6) is necessary.

Figure 1:
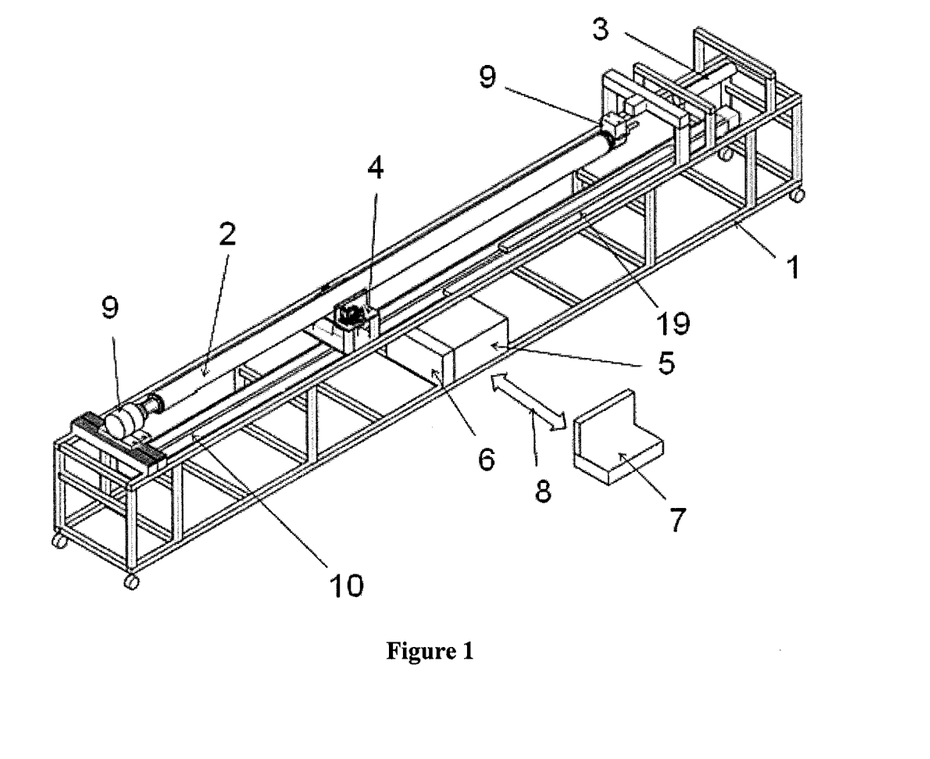
FIG. 1 represents an image of the measuring device, including the optical bench, the optical modules of the system, the external computer to control the device, and the system of communication between the device and the computer.

The two modulated light channels (12, 14) are taken by two large area multimode optical fibers to the measuring module (4) through a cable tray chain (19, FIG. 1).

For each light channel (12, 14), the spectrophotometer includes two measurements simultaneously, a direct signal measurement, either transmitted by the outer tube (13) or by the inner tube (15), depending on the channel, and a second measurement, the reflectance signal measurement. For each one of the measurements, the spectrophotometer implements two detectors (23-24, 33-34), which response spectrum overlaps in such a way that the set covers a larger spectral range than the one covered by each one of the detectors individually.

In the transmittance measuring channel (12), the light bundle at the outlet of the multimode optical fiber is collimated by means of an optical lens (20) in the range of working frequencies, and divided by a bundle splitter (21) to generate the bundle for direct measuring and the bundle for reference measuring. This lens (20) serves as the diaphragm of the optical system in order to ensure a stable transmittance measurement regarding changes in the distribution of the fiber modes. On the one hand, the direct measuring optical signal is directed through the glass tube being measured (13), and is then collected by a second lens, (22) with a larger diameter than the diaphragm of the system, in order to ensure the capture of the light bundle in its entirety regarding deviation of the bundle when passing through the curved glass of the tube (13). This second lens (22) focalizes the optical signal on two large area detectors (23) and (24) after passing through a bundle splitter (25), where it is divided and directed towards said detectors. The detectors are one Si detector and another InGaAs detector to cover the optical frequency range from 300 nm to 2,500 nm. On the other hand, the reference measuring optical signal is collected by a lens (26) with a larger diameter than the diaphragm of the system (20) in order to ensure the capture of the light bundle in its entirety. This second lens (26) focalizes the optical signal on two large area detectors (28) and (29) after passing through a bundle splitter (27), where it is divided and directed towards said detectors. The detectors are one Si detector and another InGaAs detector.

In the reflectance measuring channel (14), the light bundle at the output of the multimode optical fiber is divided by a bundle splitter (49) to generate the bundle for direct measuring and the bundle for reference measuring. A diaphragm (50) is placed in front of this bundle splitter in order to ensure a stable reflectance measurement regarding changes in the distribution of fiber modes. On the one hand, the direct measuring optical bundle is focalized by means of an optical lens (30) on the surface of the metal tube (15), and the bundle reflected in the metal tube (15) is collected by a second lens (31) with a larger diameter than the size of the bundle at this point; therefore, the capture of the entire light of the bundle regarding deviations of the bundle when reflecting on the curved metal tube is ensured This second lens (31) focalizes the optical bundle on two large area detectors (33) and (34) after passing through a bundle splitter (32), where it is divided and directed towards said detectors. The detectors are one Si detector and another InGaAs detector to cover the optical frequency range from 300 nm to 2,500 nm. On the other hand, the reference measuring optical signal is collected by a lens (35) with a larger diameter than the bundle at this point to ensure the capture of all the light of the bundle. This second lens focalizes the optical signal on two large area detectors (37) and (38) after passing through a bundle splitter (36), where it is divided and directed towards said detectors. The detectors are one Si detector and another InGaAs detector.

The analog electrical signals detected or measured (40) in the detectors of the measuring module (4) are converted into digital signals in the electronic system of data acquisition (6) by means of an analog/digital converter, and taken to the computer (7) for their processing.

The arrangement of the elements of the optical system in the measuring module is key because must enable the correct measuring of the coefficients of transmission and reflection on the same part of the tube, both at an angle of incidence and in terms of the correction of the measurements. We propose the embodiment shown in FIGS. 3, 4, 5, and 6 as the preferred embodiment to achieve the foregoing.

Figure 3:
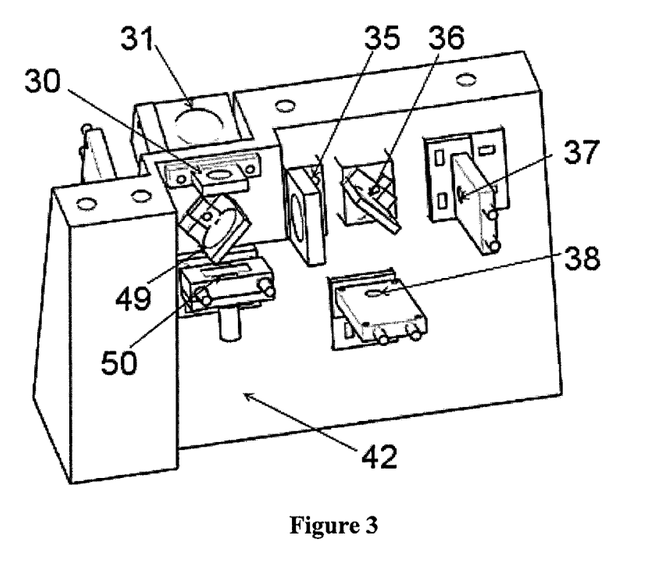
FIG. 3 represents the view of the focalization and the reference measuring face of the bench of reflection of the measuring module.
Figure 4:
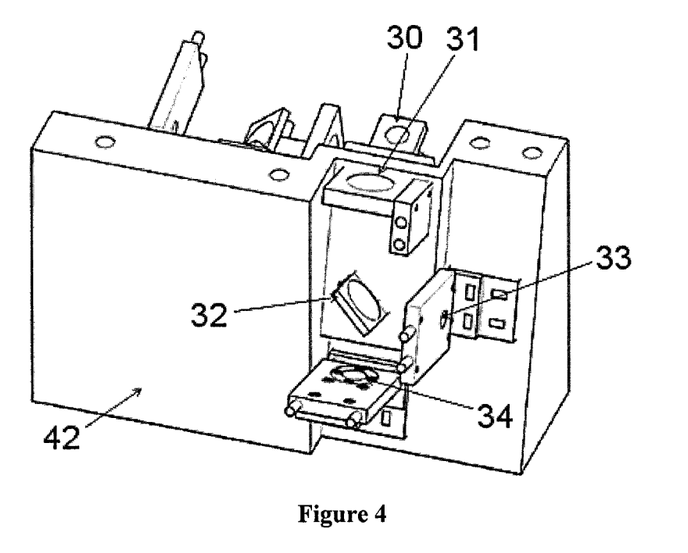
FIG. 4 represents the view of the direct measuring face of the bench of reflection of the measuring module.

The optical system that measures reflectance is placed on the reflection bench (42, FIG. 3), which is a wedge-shaped base, so that the angle of incidence of the light bundle on the metal tube is 15°. The optical elements forming the focalization system of the reflection light bundle (49, 50, 30) are placed on one side of this base, on the surface of the metal tube, together with the optical and electronic system that measures the reflection reference signal (35, 36), as shown in FIG. 3. The collection and focalization optical elements in the detectors (33, 34) of the light bundle reflected by the metal tube and the electronic elements that measure the direct reflection signal (31, 32) are placed on the other side of this base (FIG. 4).

Figure 5:
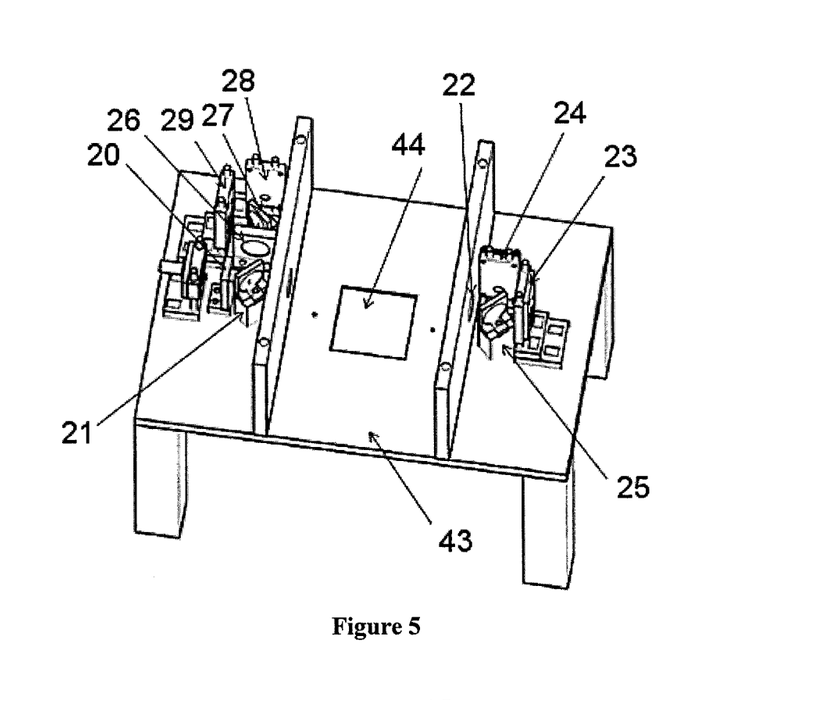
FIG. 5 represents the view of the transmission bench of the measuring module.

The optical system that measures transmittance is placed on the transmission bench (43), which is a flat base, as shown in FIG. 5. The optical elements forming the collimation system of the transmission light bundle (20, 21) are placed on one side of this base through the glass tube (13), together with the optical and electronic system that measures the transmission reference signal (26, 27, 28, 29). The collection and focalization optical elements (23, 24, 25) of the detectors of the light bundle that passes through the glass tube (13) and the electronic elements that measure the direct transmission signal are placed on the other side of this base. The tube under test (2) and a window (44) allowing the passage of the optical bundle of incidental reflection and reflected by the metal tube (15) are placed between these two optical systems.

Figure 6:
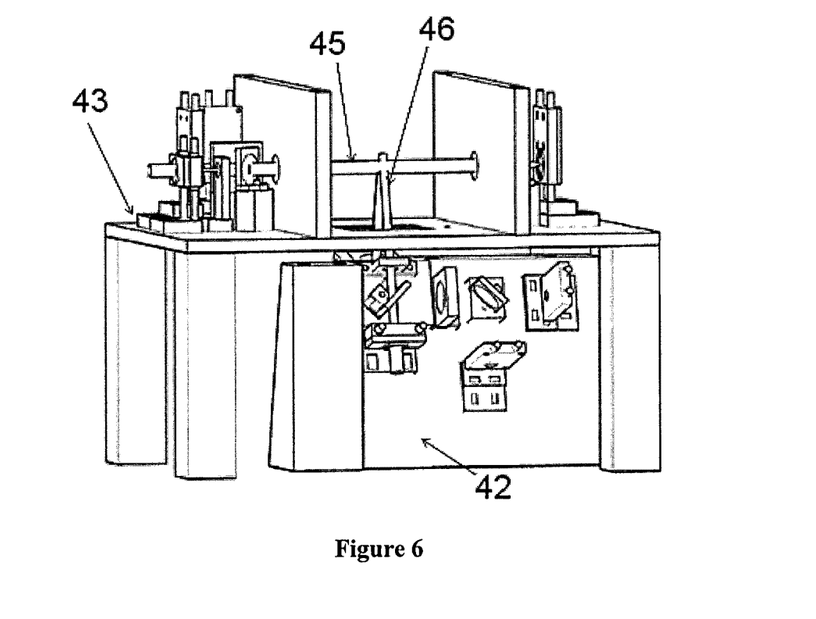
FIG. 6 represents the view of the transmission and reflection benches of the measuring module, including a representation of the light bundles for the measuring of transmission and reflection.

The systems that measure transmittance and reflectance are placed one with respect of the other in such a way that they measure the points of the glass tube (13) and the metal tube (15) that are in the same longitudinal position of the tube, as shown in FIG. 6. The optical transmittance system is placed in such a way that its axis of optical incidence (45) is transversal to the axis of the tube, and the optical reflectance system is found under it in such a way that its axis of optical incidence (46) is longitudinal to the axis of the tube. This way, greater tolerance to variations in the position of the metal tube (15) is ensured, and the correct correction of the measurement of reflectance with the attenuation of the tube by traversing the similar paths inside the glass tube (13) is also enabled.

The value of the measurement of transmittance of the glass tube (13) is taken based on the optical signals measured in the direct measuring bundle and in the reference measuring bundle, taking into account the correction due to the curvature of the glass tube (13).

The value of the measurement of reflectance of the metal tube (15) is taken based on the optical signals measured in the direct measuring bundle and in the reference measuring bundle, taking into account the correction due to the attenuation of the metal tube (15) obtained in the measuring of reflectance of the metal tube (15).

Both measurements, transmittance and reflectance, are taken simultaneously.

Depending on the wavelength, an optical filter (11) is positioned in the device to eliminate harmonics and gains in the detectors to adapt the level of the signal received in each one to the range of measurement of each detector. The photodetectors are followed by two steps of amplification, which gain depends on the value of the resistances included. One of these resistances may be a digital potentiometer, which value may be controlled via software and allows adjusting the gain of each channel at any time using the digital outputs (41) of the analog/digital conversion system (6).

A program installed in the control computer (7) allows using the commands (47) programmed in the electronic system of data acquisition and processing (6) to carry out all the functions necessary during the measuring process, including the selection of the measuring wavelength in the monochromator (16), of the filter (11) placed at the input of the monochromator, of the gains in the detectors, of the position of the measuring head along the length of the tube and of the rotation position of the tube, and the reading of the data obtained (48) for their subsequent processing and storage.

In terms of the operation method of the device, it comprises the following steps to obtain the coefficients of reflection and transmission of the tubes:

1. Positioning the tube (2) on the bench (1).
2. Turning on the white light lamp (17) of the device.
3. Selecting the measuring points of the tube and the measuring wavelengths in the system.
4. The device will position the rotation of the tube and the position of the measuring module (4) at each one of the configured measuring points in a sequential manner. The monochromator (16) carries out the selected spectral scanning at each one of these points. The data obtained in the transmission and reflection detectors for each wavelength is normalized with its reference measurement. Depending on the wavelength, an optical filter (11) is positioned in the device to eliminate harmonics and gains in the detectors to adapt the level of the signal received in each one to the range of measurement of each detector.
5. The coefficient of transmission and reflection of the tubes for each wavelength being measured are then obtained; this final value of the coefficients is also obtained by reference to a known framework.
6. The values corresponding to the framework (3) are stored in the device and were previously obtained by means of a calibration process that requires the use of a tube (3) with known coefficients of transmission and reflection. This calibration is carried out following steps 2 to 4 in the same procedure.

Therefore, the industrial application of this device is the characterization of absorbing tube-type surfaces installed in solar collectors, normally composed of two concentric tubes: an inner metal tube, which coefficient of reflection is of interest, and an outer glass tube, which coefficient of transmission is of interest. Even though its design is specific for this type of surfaces, it may be used in any type of application with similar characteristics.

The invention claimed is:
1. A spectrophotometer for automated optical characterization of solar collector tubes, the solar collector tubes being formed by an inner metal tube and an outer glass tube, wherein the spectrophotometer is placed on a measuring bench, and wherein the solar collector tube to be characterized is placed in the measuring bench, the spectrophotometer comprising:
- a light source that generates light for measurement of a coefficient of transmission of the outer glass tube and a coefficient of reflection of the inner metal tube of the solar collector tube in the measuring bench;
- a measuring module comprising two or more lenses and first and second light detectors, the measuring module receiving light from the light source and the two or more lenses positioned such that a first portion of the received light is directed through the outer glass tube to the first light detector and a second portion of the received light is simultaneously directed to the surface of the inner metal tube and to the second light detector after reflecting from the surface of the inner metal tube, the first and second light detectors producing respective signals indicating the intensity of light falling on the light detectors;
- a mechanical system of linear displacement that displaces the measuring module in an automated manner along the length of the solar collector tube, the spectrophotometer measuring the coefficient of reflection of the inner metal tube and the coefficient of transmission of the outer glass tube at multiple points along the length of the solar collector tube;
- an electronic system of data acquisition and processing with an analog/digital converter, the electronic system of data acquisition receiving the output signals from the first and second light detectors;
- a computer for controlling the spectrophotometer and processing the measured data; and
- a system of communication between the electronic system of data acquisition and the computer.

2. The spectrophotometer for automated optical characterization of solar collector tubes according to claim 1, wherein the measuring bench further comprises a mechanical system of solar collector tube rotation.

3. The spectrophotometer for automated optical characterization of solar collector tubes according to claim 1, wherein the light source comprises a white light source, the spectrophotometer further comprising a set of filters at the output of the light source, a monochromator at the output of the filters that selects the desired wavelength on the light signal, two multimode optical fibers at the output of the monochromator that generate two optical channels and a modulation system by chopper of the optical signal of the two channels.

4. The spectrophotometer for automated optical characterization of solar collector tubes according to claim 1, wherein the light source and the measuring module are connected by means of two large area multimode optical fibers placed in a cable tray chain.

5. The spectrophotometer for automated optical characterization of solar collector tubes according to claim 1, wherein the measuring module receives the light from the light source by means of two multimode optical fibers, a first of the two multimode optical fibers carrying light from the light source, including the first portion of the received light, used in measuring the coefficient of transmission of the outer glass tube and the second of the two multimode optical fibers carrying light from the light source, including the second portion of the received light, used in measuring the coefficient of reflection of the inner metal tube, the measuring module further comprising:
- a transmission reference light detector positioned to receive a third portion of the received light, the third portion of the received light taken from the first of the two multimode optical fibers and directed to the transmission reference light detector without having passed through the outer glass tube; and
- a reflectance reference light detector positioned to receive a fourth portion of the received light, the fourth portion of the received light taken from the second of the two multimode optical fibers and directed to the reflectance reference light detector without having reflected from the inner metal tube;
- wherein outputs of the transmission reference light detector and the reflectance reference light detector are measured simultaneously with the output signals of the first and second light detectors.

6. The spectrophotometer for automated optical characterization of solar collector tubes according to claim 5, further comprising:
- an optical lens positioned to collimate an optical bundle output by the first of the multimode optical fibers and serving as a diaphragm of the system behind the output of the first multimode optical fiber in the measuring of transmittance; and
- a bundle splitter positioned to receive the collimated light from the lens and to generate an optical bundle for direct measuring and an optical bundle for reference measuring.

7. The spectrophotometer for automated optical characterization of solar collector tubes according to claim 6, wherein a second lens with a larger diameter than the diaphragm of the system is installed for direct measuring, which captures all the light of the bundle after passing through the curved glass of the outer glass tube, and a bundle splitter that divides and focalizes the optical signal onto two large area detectors is installed behind the lens.

8. The spectrophotometer for automated optical characterization of solar collector tubes according to claim 6, wherein a lens with a larger diameter than the diaphragm of the system is installed for reference measuring, which focalizes the optical signal on two large area detectors after passing through a bundle splitter, where the optical bundle is divided and directed towards said two large area detectors.

9. The spectrophotometer for automated optical characterization of solar collector tubes according to claim 5, wherein a diaphragm is placed behind the output of the multimode optical fiber in the measuring of reflectance and a bundle splitter is installed to generate an optical bundle for direct measuring and an optical bundle for reference measuring.

10. The spectrophotometer for automated optical characterization of solar collector tubes according to claim 9, wherein an optical lens is installed that focalizes the optical bundle on the surface of the metal tube, a second lens with a larger diameter than the size of the optical bundle at this point is positioned to receive the optical bundle after the optical bundle reflects from the inner metal tube, and the second lens focalizes the optical bundle on two large area detectors after passing through a bundle splitter, where the optical bundle is divided and directed towards said two large area detectors.

11. The spectrophotometer for automated optical characterization of solar collector tubes according to claim 9, wherein a lens with a larger diameter than the diaphragm of the system is installed for reference measuring, which focalizes the optical signal on two large area detectors after passing through a bundle splitter, where the optical bundle is divided and directed towards said two large area detectors.

12. The spectrophotometer for automated optical characterization of solar collector tubes according to claim 7, wherein the detectors used have a spectrum of response that overlaps in such a way that the set covers a larger spectral range than the one covered by each one of the detectors individually.

13. The spectrophotometer for automated optical characterization of solar collector tubes according to claim 12, wherein in each pair of detectors, one detector is Si and the other is InGaAs in order to cover the optical frequencies range from 300 nm to 2,500 nm.

14. The spectrophotometer for automated optical characterization of solar collector tubes according to claim 12, wherein the light detectors are followed by two steps of amplification based on resistances.

15. The spectrophotometer for automated optical characterization of solar collector tubes according to claim 14, wherein the resistances are digital potentiometers whose values can be controlled via software.

16. The spectrophotometer for automated optical characterization of solar collector tubes according to claim 1, wherein the optical system that measures reflectance is placed on a reflection bench comprising a wedge-shaped base.

17. The spectrophotometer for automated optical characterization of solar collector tubes according to claim 16, wherein the wedge is such that the angle of incidence of the optical bundle in the metal tube is 15°.

18. The spectrophotometer for automated optical characterization of solar collector tubes according to claim 16, wherein all optical elements involved in directing the reflection optical bundle onto the surface of the metal tube, together with optical and electronic elements involved in measuring a reference reflection signal, are placed on a first side of the reflection bench, and all optical elements involved in the collection of the optical bundle reflected by the metal tube and electronic elements for measuring a direct reflection signal are placed on a second side of the reflection bench opposite the first side.

19. The spectrophotometer for the automated optical characterization of solar collector tubes according to claim 1, wherein the optical system that measures transmittance is placed on a transmission base, wherein the transmission base has a flat base.

20. The spectrophotometer for the automated optical characterization of solar collector tubes according to claim 19, wherein all optical elements involved in directing the transmission light bundle through the outer glass tube, together with optical and electronic elements involved in measuring a reference transmission signal, are placed on a first side of a transmission bench, and optical elements involved in the collection of the optical bundle that passes through the outer glass tube and electronic elements that measure a direct transmission signal are placed on a second side of the transmission bench opposite the first side.

21. The spectrophotometer for automated optical characterization of solar collector tubes according to claim 20, wherein a solar collector tube under test and a window allowing the passage of the optical bundle of incidental reflection and reflected by the metal tube are placed between the two sides of the transmission bench.

22. The spectrophotometer for automated optical characterization of solar collector tubes according to claim 21, wherein the first portion of the received light is directed through the outer glass tube transversely to the axis of the solar collector tube under test and the second portion of the received light is directed to the surface of the inner metal tube from underneath the solar collector tube under test, in such a way that the axis of optical incidence of the second portion of the received light onto the metal tube is longitudinal to the axis of the solar collector tube under test.

23. The spectrophotometer for automated optical characterization of solar collector tubes according to claim 1, wherein the electronic system of data acquisition and processing has an analog/digital converter that receives the analog electrical signals detected in the measuring module and takes the analog electrical signals to the computer for processing.

24. The spectrophotometer for automated optical characterization of solar collector tubes according to claim 1, wherein the computer has a program installed that allows using commands programmed in the electronic system of data acquisition and processing to carry out all the functions necessary during the measuring process, including the selection of the measuring wavelength in a monochromator, of the filter placed at the input of the monochromator, of the gains in the first and second light detectors, of the position of the measuring module along the length of the a solar collector tube and of a rotation position of the tube, and the reading of the data obtained for subsequent processing and storage of the data.

25. A method of operation of spectrophotometer according to claim 1, the method comprising the following steps to obtain the coefficients of reflection and transmission of the solar collector tube:
1) positioning the solar collector tube on the measuring bench;
2) turning on the light source;
3) selecting multiple points along the length of the solar collector tube at which to measure the solar collector tube and the measuring wavelengths in the spectrophotometer;
4) rotating the tube and positioning the measuring module at each one of the selected measuring points along the length of the solar collector tube in a sequential manner; carrying out scanning of the solar collector tube at each one of the selected points and wavelengths; normalizing the data obtained in the first and second light detectors for each wavelength with a respective reference measurement; depending on the wavelength, positioning an optical filter in the spectrophotometer to eliminate harmonics and gains in the light detectors to adapt the level of the signal received in each one to the range of measurement of each of the light detectors;
5) obtaining the coefficient of transmission and reflection of the solar collector tube for each wavelength measured, this final value of the coefficients also being obtained by reference to a known standard; and
6) storing values corresponding to the standard in the spectrophotometer that were previously obtained by means of a calibration process that requires the use of a solar collector tube with known coefficients of transmission and reflection, where the calibration process is carried out following steps 2 to 4.

* * * * *